(12) United States Patent
DiPalma

(10) Patent No.: US 6,689,933 B1
(45) Date of Patent: Feb. 10, 2004

(54) ABSORBENT ARTICLE HAVING VERTICALLY ORIENTATED ABSORBENT MEMBERS

(75) Inventor: Joseph DiPalma, Neenah, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 09/396,716

(22) Filed: Sep. 15, 1999

(51) Int. Cl.$^7$ ................................. A61F 13/15
(52) U.S. Cl. ................... 604/367; 604/385.01
(58) Field of Search ................. 604/358, 367, 604/378, 385.01, 385.101

(56) References Cited

U.S. PATENT DOCUMENTS

| | | |
|---|---|---|
| 3,668,054 A | 6/1972 | Stumpf |
| 3,838,694 A * | 10/1974 | Mesek ............. 128/287 |
| 3,903,890 A * | 9/1975 | Mesek et al. ......... 128/287 |
| 3,965,904 A * | 6/1976 | Mesek et al. ......... 128/284 |
| 4,015,604 A | 4/1977 | Csillag |
| 4,027,672 A | 6/1977 | Karami |
| 4,100,324 A | 7/1978 | Anderson et al. |
| 4,467,012 A | 8/1984 | Pedersen et al. |
| 4,627,848 A | 12/1986 | Lassen et al. |
| RE32,649 E | 4/1988 | Brandt et al. |
| 4,735,624 A | 4/1988 | Mazars |
| 4,798,603 A | 1/1989 | Meyer et al. |
| 4,908,026 A | 3/1990 | Sukiennik et al. |
| 5,181,563 A | 1/1993 | Amaral |
| 5,190,533 A | 3/1993 | Blackburn |
| 5,248,309 A | 9/1993 | Serbiak et al. |
| 5,336,552 A | 8/1994 | Strack et al. |
| 5,360,504 A | 11/1994 | Fell et al. |
| 5,364,382 A | 11/1994 | Latimer et al. |
| 5,399,175 A * | 3/1995 | Glaug et al. ............. 604/385.01 |
| 5,401,267 A | 3/1995 | Couture-Dorschner et al. |
| 5,423,786 A | 6/1995 | Fung et al. |
| 5,460,623 A | 10/1995 | Emenaker et al. |
| 5,466,232 A | 11/1995 | Cadieux et al. |
| H1511 H | 12/1995 | Chappell et al. |
| 5,490,846 A | 2/1996 | Ellis et al. |
| 5,505,719 A | 4/1996 | Cohen et al. |
| 5,506,277 A | 4/1996 | Griesbach, III |
| H1585 H | 8/1996 | Ahr |
| 5,613,962 A | 3/1997 | Kenmochi et al. |
| 5,649,916 A | 7/1997 | DiPalma et al. |
| 5,656,361 A | 8/1997 | Vogt et al. |
| 5,672,165 A * | 9/1997 | Belecky et al. ............. 604/383 |
| 5,683,374 A | 11/1997 | Yamamoto et al. |
| 5,830,202 A | 11/1998 | Bogdanski et al. |
| 5,833,678 A | 11/1998 | Ashton et al. |
| 5,843,063 A | 12/1998 | Anderson et al. |
| 5,853,402 A | 12/1998 | Faulks et al. |
| 5,869,171 A | 2/1999 | Shiveley et al. |
| 5,879,343 A | 3/1999 | Dodge, II et al. |

FOREIGN PATENT DOCUMENTS

| | | | |
|---|---|---|---|
| EP | 339461 | 11/1989 | |
| EP | 366 079 | 5/1990 | |
| EP | 586 936 | 3/1994 | |
| EP | 0 687 453 A1 * | 12/1995 | ........... A61F/13/15 |
| EP | 0 815 817 A1 * | 7/1998 | ........... A61F/13/15 |
| WO | 98/56326 | 12/1998 | |
| WO | 99/32165 | 7/1999 | |

* cited by examiner

*Primary Examiner*—Weilun Lo
*Assistant Examiner*—Michele Kidwell
(74) *Attorney, Agent, or Firm*—Pauley Petersen & Erickson (57) ABSTRACT

Absorbent pad assemblies and articles are provided which include adjacent noncontinuous vertically orientated absorbent members, horizontally displaced relative to each other along the entire vertical heights thereof and forming a vertically disposed surface interface therebetween.

32 Claims, 5 Drawing Sheets

ABSORBENT ARTICLE HAVING VERTICALLY ORIENTATED ABSORBENT MEMBERS

FIELD OF THE INVENTION

This invention relates generally to absorbent articles for absorbing body fluids and exudates. More particularly, the present invention relates to absorbent pad assemblies and associated absorbent articles having improved leak prevention and/or fluid flow control.

BACKGROUND OF THE INVENTION

A wide variety of types of structures are known in the art for use in or as absorbent articles, particularly disposable absorbent articles, used to collect various body fluids and exudates. Commercial absorbent articles include diapers, adult incontinence products, sanitary napkins and bandages. Disposable products of this type generally comprise components for receiving, absorbing and retaining fluids. Typically, the components of such articles include a liquid permeable topsheet, an absorbent core and a liquid impermeable backsheet.

The components of typical absorbent articles are commonly plied or arranged in a horizontal fashion with a major planar surface facing the fluid intake area, e.g., the body of the wearer. In such absorbent articles, the nature or make-up of the fluid communicating therethrough can and typically will change as such fluid traverses though the horizontal ply or plies. Thus, such absorbent articles may experience undesirable horizontal dependency between components. Further, the fibers which customarily make-up the absorbent core are often orientated randomly with fibers within a mat in a lateral neighboring arrangement such that the fluid intake typically wicks in a radial fashion or pattern.

One of the main objectives in the development of absorbent articles is to increase, improve or maximize utilization of the absorbent capacity of the article. In general, products of the type described above typically distribute liquids deposited on the topsheet in a circular pattern. Since such structures generally have a length that exceeds their width, such liquid distribution may undesirably result in the fluids, e.g., exudates, reaching the longitudinal side edges of the absorbent article prior to the desirable utilization of the absorbent capacity at the end regions of the absorbent article. As will be appreciated, such occurrence may undesirably increase the possibility or likelihood of leakage from the sides of the article despite the availability of unutilized or underutilized absorbent capacity in the end regions of the absorbent article.

Moreover, such absorbent articles can and may be subjected to a wide range of conditions and applications such as due to factors inherent or related to the environment in which the article is utilized. Thus, the fluids and exudates which may need to be absorbed thereby may vary in properties or parameters such as including flow rate as well as form, phase or composition. For example, exudates may be multiphasic and heterogeneous, such as in the case of menses which may include red blood cells, mucin, plasma and tissue debris, for example.

Sanitary napkins (also referred to as catamenial pads), feminine pads, overnight pads, panty liners and panty shields are designed to be worn by a female to absorb menses and other body fluids discharged before, during and after a menstrual period. Sanitary napkins are external devices which are designed to be aligned approximate the pudendum region of a human body and are generally held in position by being adhesively or mechanically attached to an undergarment. Sanitary napkins also typically differ from panty liners and panty shields in several notable ways. Sanitary napkins are generally larger in size and have a more defined 3-dimensional configuration, are thicker in caliper and have a greater fluid capacity than panty liners or panty shields.

In view of the desire to provide increased comfort to the wearer and to minimize the appearance of the presence of such absorbent articles there is an ongoing demand and need for smaller or less bulky absorbent articles. Thus, there is a need and a demand for improved absorbent pad assemblies and absorbent articles such as may result in more complete utilization of the absorbent capacity thereof and such as may more effectively and efficiently respond to the possibly wide range of operating and performance conditions to which such assemblies and articles can be exposed.

SUMMARY OF THE INVENTION

A general object of the invention is to provide an improved absorbent pad assembly and absorbent article.

A more specific objective of the invention is to overcome one or more of the problems described above.

The general object of the invention can be attained, at least in part, through a specific absorbent pad assembly. In accordance with one preferred embodiment, the absorbent pad assembly includes at least first and second adjacent noncontinuous vertically orientated absorbent members. Each of the first and second absorbent members have a vertical height. The first and second absorbent members are horizontally displaced relative to each other along the entire vertical heights thereof and form a vertically disposed surface interface therebetween.

The prior art generally fails to provide absorbent pad assemblies and absorbent articles which make as complete or full utilization of the absorbent capacity thereof as may be desired. The prior art also generally fails to provide absorbent pad assemblies and absorbent articles which can respond to the possibly wide range of operating and performance conditions to which such assemblies and articles can be exposed and to do so in an as effective and efficient a manner as may be desired.

The invention further comprehends a specific absorbent article. In accordance with one preferred embodiment of the invention, such an absorbent article includes an absorbent pad assembly. The absorbent pad assembly includes at least first, second and third generally planar absorbent members, each having a vertical height and wherein at least the first and second absorbent members comprise materials of different chemical compositions. The first and second absorbent members are horizontally displaced relative to each other along the entire vertical heights thereof and form a first vertically disposed surface interface therebetween. The second and third absorbent members are horizontally displaced relative to each other along the entire vertical heights thereof and form a second vertically disposed surface interface therebetween.

The invention still further comprehends, in accordance with another embodiment of the invention, an absorbent article having a contact surface. The absorbent article includes a pad assembly. The pad assembly includes at least first and second adjacent noncontinuous absorbent members of different absorbency. The first and second absorbent members are generally perpendicularly disposed relative to the contact surface and form a surface interface therebetween also generally perpendicularly disposed relative to the contact surface.

Another aspect of the invention relates to specific methods for forming such and similar absorbent structures. In accordance with one embodiment, one such method involves adjacently disposing at least first and second absorbent members and orientating the adjacently disposed first and second absorbent members to each have a ratio of horizontal width to vertical height of no more than about 10:1.

In accordance with another embodiment, a method for forming an absorbent pad assembly is provided. Such a method involves horizontally layering at least first and second absorbent members and vertically reorientating the horizontally layered first and second absorbent members.

In accordance with another embodiment, a method for improving the fluid management by an absorbent article which includes a liquid pervious cover, a liquid impervious backsheet and an absorbent pad assembly disposed between the cover and the backsheet is provided. The method involves the utilization of an absorbent pad assembly including at least first and second adjacent noncontinuous vertically orientated absorbent members, each of the first and second absorbent members having a vertical height with the first and second absorbent members horizontally displaced relative to each other along the entire vertical heights thereof and forming a vertically disposed surface interface therebetween. As described in greater detail below, one particular form of such an absorbent article is a sanitary napkin.

As used herein, references to "absorbent article(s)" are to be understood to refer to products such as diapers, sanitary napkins, training pants, incontinent garments, overnight pads, panty liners, under arm shields and the like, which are used to absorb body fluids and exudates, such as urine, menses, blood, perspiration and other excrements discharged by the body.

Further, references herein to absorbent members as being "vertically orientated" are to be understood to refer to the general disposition of the member and are in general reference relative to the body contacting surface or face of the absorbent article itself. In general, vertically orientated absorbent members are to be understood as having a ratio of horizontal width to vertical height of no more than about 10:1, preferably no more than about 5:1 and, more preferably about 1:1 or less.

References herein to adjacent absorbent members as being "noncontinuous" are to be understood to refer to such adjacent absorbent members as forming or having a surface interface therebetween. As will be appreciated, such a surface interface may, in practice, serve to hinder, prevent or avoid fluid passage between or from one to another of the adjacent absorbent members. As will be appreciated and as described in greater detail below, adjacent absorbent members will preferably differ in one or more property or characteristic such as chemical composition or construction such as fiber orientation or thickness, for example. Other effective properties or characteristics by which adjacent absorbent members may differ will be apparent to those skilled in the art and guided by the teachings herein provided.

References herein to adjacent absorbent members as forming a "surface interface" therebetween are to be understood as referring to the formation between adjacent members of a surface at which the adjacent members contact or are in proximity to each other.

References herein to "contact surface" are to be understood as referring to that surface of the absorbent member, pad assembly, article or the like with which the fluid to be absorbed initially contacts.

Other objects and advantages will be apparent to those skilled in the art from the following detailed description taken in conjunction with the appended claims and drawings.

DETAILED DESCRIPTION OF THE PRESENTLY PREFERRED EMBODIMENTS

The present invention, as is described in more detail below, provides an improved absorbent pad assembly and absorbent article as well as a method of forming such absorbent products.

Figure 1:
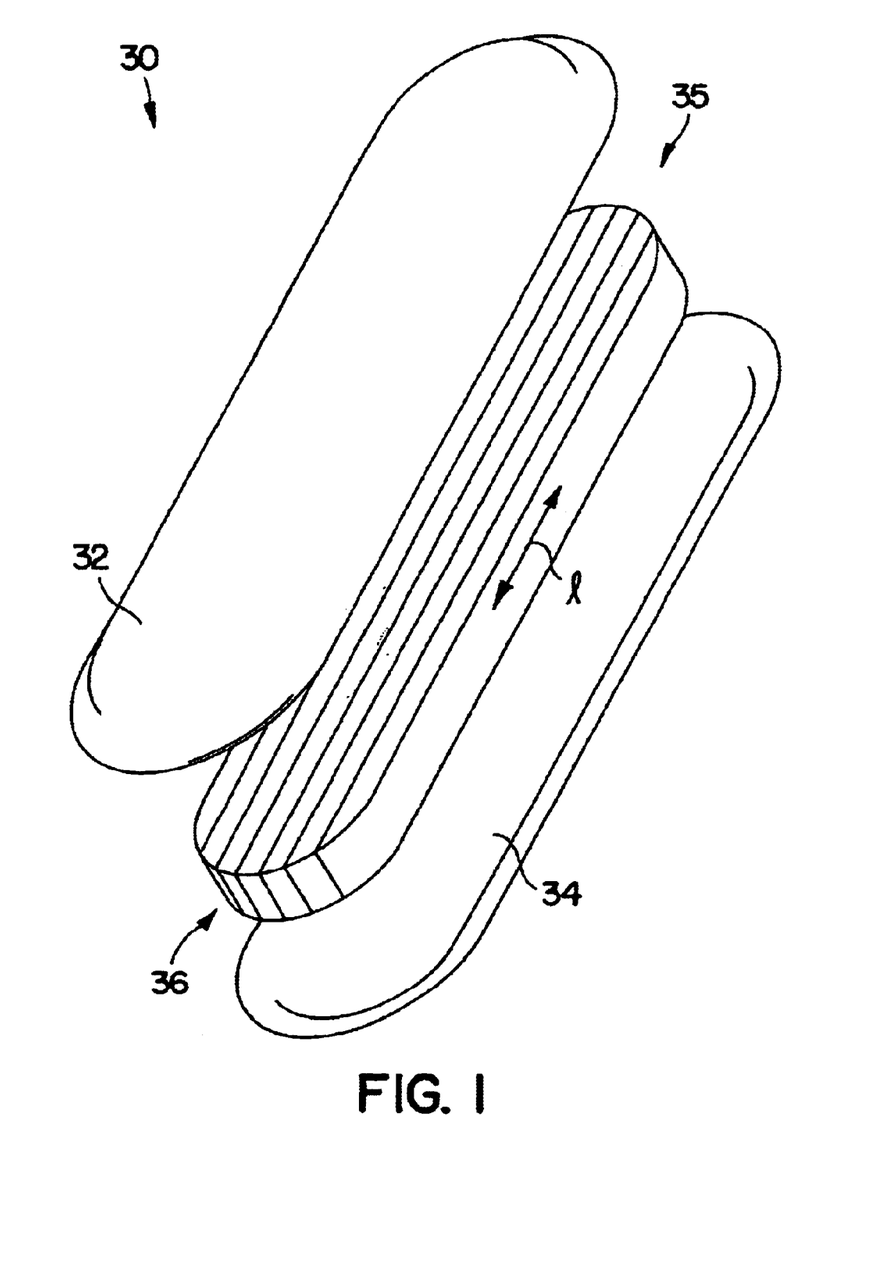
FIG. 1 is an exploded perspective view of an absorbent article having a pad assembly in accordance with one preferred embodiment of the invention.
Figure 2:
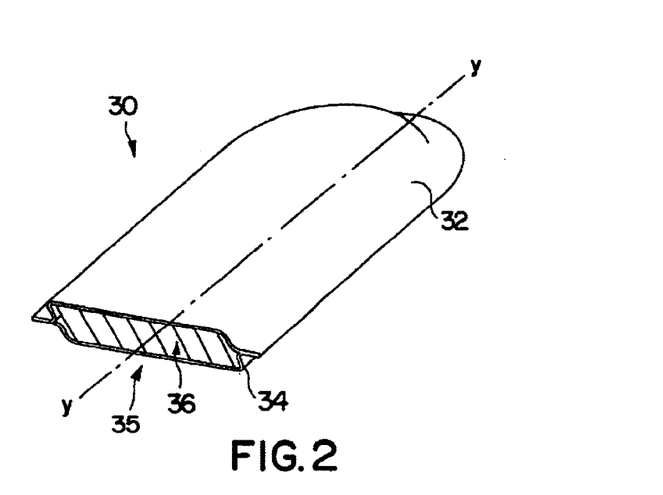
FIG. 2 is a partial sectional perspective view of the absorbent article shown in FIG. 1.
Figure 3:
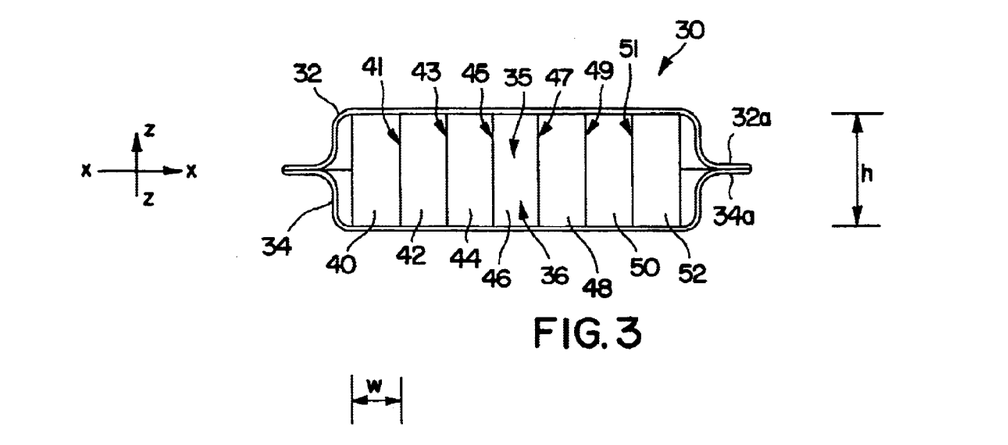
FIG. 3 is a simplified sectional side view of the absorbent article shown in FIGS. 1 and 2.

Referring initially to FIGS. 1–3, there is illustrated an absorbent article, generally designated by the reference numeral 30, in accordance with one embodiment of the invention and which article is capable of absorbing body fluid. The absorbent article can be a diaper, training pant, sanitary napkin, panty liner, overnight pad, incontinence garment, underarm shield or other type of absorbent product capable of absorbing one or more bodily fluid such as urine, menses, blood, perspiration, excrement or the like. As will be appreciated, such an absorbent article will typically be disposable in the nature. While the absorbent article 30 will be described herein in terms of a feminine care product such as a sanitary napkin, it is to be understood that the broader practice of the invention is not necessarily so limited and that the invention can, if desired be practiced in or in association with other types or forms of absorbent articles such as identified above.

The absorbent article 30 comprises a generally liquid pervious topsheet or cover 32 on the body-side surface of the article, a generally liquid impervious backsheet or baffle 34 on the opposing garment-facing side of the article and an absorbent core 35, disposed and enclosed therebetween.

It will be appreciated that absorbent articles such as feminine care products such as sanitary napkins may typically include additional standard or usual features such as relating to the positioning or placement of the article when in use. For example, certain sanitary napkin designs incorporate side flaps, sometimes referred to as "wings," such as can be helpful in preventing fluid flow from the sides of the napkin. Another example of such a feature is the inclusion or presence of an adhesive at or about the garment facing region face of the backsheet. Such adhesive surface of the article can be covered by a release paper or the like, as is known in the art, prior to use such as when in a packaged state. As such features are standard or common, are well known to those skilled in that art and form no part of the broader invention, they will not be shown or described in great detail herein.

The topsheet or cover 32 is generally designed to contact the body of the user and generally forms the contact surface of the absorbent article 30. In practice, the topsheet 32 can be constructed of a woven or nonwoven material, from synthetic or natural materials and desirably should be easily penetrated by body fluid. Suitable materials include bonded carded webs of polyester, polypropylene, polyethylene, nylon or other heat-bondable fibers. Other polyolefins, such as copolymers of polypropylene and polyethylene, linear low-density polyethylene, finely perforated film webs and net material also work well. The topsheet 32 may also be constructed of a thermoplastic film which contains apertures and is flanked on one or both sides by a nonwoven material. Such an embodiment may desirably present a relatively soft feel against a user's thigh while allowing the rapid passage therethrough of body fluid.

The backsheet or baffle 34 is generally liquid impermeable and is designed to face the inner face, e.g., the crotch portion, of an undergarment (not shown). The backsheet 34 may desirably be designed to permit the passage of air or vapor out of the absorbent article 30 while preventing or blocking the passage of fluids therethrough. As will be appreciated, the backsheet 34 can be made of any suitable material capable of providing or having the above-identified properties or characteristics. For example, suitable materials may include a microembossed polymeric film such as of polyethylene or polypropylene.

As will be appreciated, the topsheet 32 and the backsheet 34 can be placed coextensive, in face-to-face contact around or about the absorbent core 35. Further, the topsheet 32 has a periphery 32a and the backsheet 34 has a periphery 34a which are desirably joined or sealed together by use of an adhesive, by heat sealing ultrasonics or other suitably selected techniques such as are known to those skilled in the art.

The absorbent core 35 is formed at least in part by an absorbent pad assembly 36. As shown in FIGS. 2 and 3, the absorbent pad assembly is a three-dimensional structure having a horizontal axis X—X, a vertical axis Z—Z and a length axis Y—Y. The absorbent pad assembly 36 includes adjacent noncontinuous vertically orientated absorbent members 40, 42, 44, 46, 48, 50, and 52, respectively. In practice, absorbent pad assemblies in accordance with the invention will typically include at least two and, preferably, at least three, such adjacent noncontinuous vertically orientated absorbent members. As will be appreciated, the specific number or nature of the absorbent members included within an absorbent pad assembly in accordance with the invention can generally be selected by one skilled in the art and guided by the teachings herein provided in order to satisfy the required or desired performance criteria of the particular application to which the assembly under consideration is directed.

As shown, the adjacent absorbent members 40 and 42 form a vertically disposed surface interface 41 therebetween. Similarly, the adjacent absorbent members 42 and 44 form a vertically disposed surface interface 43 therebetween, the adjacent absorbent members 44 and 46 form a vertically disposed surface interface 45 therebetween, the adjacent absorbent members 46 and 48 form a vertically disposed surface interface 47 therebetween, the adjacent absorbent members 48 and 50 form a vertically disposed surface interface 49 therebetween, and the adjacent absorbent members 50 and 52 form a vertically disposed surface interface 51 therebetween. As will be appreciated, the surface interfaces 41,43, 45,47,49, and 51 are each generally perpendicularly disposed relative to the contact surface of the absorbent article 30.

As shown, adjacent absorbent members are horizontally displaced relative to each other along the entire vertical heights thereof. That is, adjacent absorbent members generally do not have any portions having the same placement on the X—X axis. For example, no portion of absorbent member 40 underlies or has the same X—X axis placement as a portion of adjacent absorbent member 42.

Each of the absorbent members 40,42,44,46,48,50 and 52 is generally planar and perpendicularly disposed relative to the contact surface of the absorbent article 30. The absorbent members each have a vertical height (h), a horizontal width (w) and a longitudinal length (l). As will be appreciated, the specific height, width and length of the absorbent members used will generally be selected to satisfy the particular requirement of the application to which such absorbent members are to be applied. Absorbent members used in the practice of the invention will generally have a width of in the range of about 0.03 mm to no more than about 20 mm and a height of about 1 mm to about 15 mm. In practice, however, absorbent members used in the invention will typically have a width of no more than about 8 mm (e.g., in the range of about 0.5 mm to about 8 mm) and, preferably, will have a width of no more than about 5 mm (e.g., in the range of about 1 mm to about 5 mm).

In accordance with the invention, the absorbent members are advantageously arranged such as to generally provide a much lower width to height ratio than normally obtained or realized in absorbent articles such as sanitary napkins. Such an absorbent member arrangements, with a significantly lower width to height ratios, promote wicking in the directions of the Y—Y and Z—Z axis since fluid is more likely to travel to fibers in close proximity rather than span across vertically disposed surface interfaces formed between the adjacent absorbent members.

Further, the vertical orientation of adjacent absorbent members in accordance with the invention permits the design of absorbent pad assemblies and associated absorbent articles which facilitate the use of selected and multiple absorbent materials in close proximity to the fluid intake area. As will be appreciated by those skilled in the art, at least certain absorbent articles, including various feminine care products such as including sanitary napkins, may be required to satisfactorily perform in association with fluids having variable or a wide range of possible or likely constituents. Thus, the subject invention development of absorbent pad assemblies and absorbent articles wherein possible multiple different absorbent materials can be conveniently placed in close proximity to the fluid intake area is a significant advancement in the art. Also, the absorbent pad assemblies and absorbent articles of the invention can advantageously avoid complications such as relating to horizontal dependency, such as described above.

In accordance with one preferred embodiment of the invention, absorbent members preferably have a width to height ratio of less than 1 in order to more fully realize the benefits of the specifically orientated absorbent members of the subject absorbent pad assembly and absorbent article.

While the height and width of each of the absorbent members for the absorbent pad assembly 36 are the same, it is to be understood that the broader practice of the invention is not necessarily so limited and that the invention can, if desired, be practiced in conjunction with absorbent members which differ in height, width or both.

Absorbent members for use in the practice of the invention can be fabricated or formed of various suitable absorbent materials such as are known in the art. For example, selected absorbent members for use in the practice of the invention can be fabricated or formed of various hydrophilic types of natural or synthetic fibers including cellulose fibers, surfactant-treated meltblown fibers, wood pulp fibers, regenerated cellulose, cotton fibers or a blend of other fibers.

Absorbent member materials of construction can include a material described in U.S. Pat. No. 4,100,324 and generally known as coform. Coform is available from the Kimberly-Clark Corporation located in Neenah, Wis. and is generally a nonwoven material made up of an airform matrix of thermoplastic polymeric fibers and a multiplicity of individualized wood pulp fibers, and has a fabric-like finish. The thermoplastic fiber polymers generally have an average diameter of less than 10 microns with the individualized wood pulp fibers dispersed throughout the matrix and serving to space these microfibers from each other. Such material can be formed by initially utilizing the primary air stream with the meltblown microfibers and the secondary air stream containing wood pulp fibers and merging the two streams under turbulent conditions to form an integrated air stream along a forming surface.

In certain embodiments, the use of absorbent materials in the nature of surge materials may be desired. Various woven fabrics and nonwoven webs can be used to construct surge materials. For example, a surge material may be a nonwoven fabric layer composed of a meltblown or spunbond web of polyolefin filaments. Such nonwoven fabric layers may include conjugate, biconstituent and homopolymer fibers of staple or other lengths and mixtures of such fibers with other types of fibers. The surge material also can be a bonded carded web or an airlaid web composed of natural and/or synthetic fibers. The bonded carded web may, for example, be a powder bonded carded web, an infrared bonded carded web, or a through-air bonded carded web. The bonded carded webs can optionally include a mixture or blend of different fibers, and the fiber lengths within a selected web may range from about 3 mm to about 60 mm.

Examples of particular surge materials may be found in U.S. Pat. No. 5,490,846 to Ellis et al. and in U.S. Pat. No. 5,364,382 to Latimer. Surge materials may be composed of a substantially hydrophobic material, and the hydrophobic material may optionally be treated with a surfactant or otherwise processed to impart a desired level of wettability and hydrophilicity.

Another possible suitable absorbent material is the material known as PRISM available from Kimberly-Clark Corporation. A description of PRISM is taught in U.S. Pat. No. 5,336,552 to Strack et al. and the disclosure of that patent is incorporated by reference herein in its entirety. PRISM is generally the nonwoven fabric and comprises extruded multicomponent polymeric strands including first and second polymeric components arranged in substantially distinctive zones across the cross-section of the multicomponent strands and extending continuously along the length of the multicomponent strands. Preferably, the strands are continuous filaments which may be formed by spunbonding techniques. The second component of the strands constitutes at least a portion of the peripheral surface of the multicomponent strands continuously along the length of the multicomponent strands and includes a blend of a polyolefin and an ethylene alkyl acrylate copolymer. Bonds between the multicomponent strands may be formed by the application of heat. More specifically, the first polymeric component of the multicomponent strands is present in an amount of from about 20 to about 80 percent by weight of the strands and the second polymeric component is present in an amount from about 80 to about 20 percent by weight of the strands. Preferably, the first polymeric component of the multicomponent strands is present in an amount of from about 40 to about 60 percent by weight of the strands and the second polymeric component is present in an amount from about 60 to about 40 percent by weight of the strands.

The term "strand" as used herein refers to an elongated extrudate formed by passing a polymer through a forming orifice such a die. Strands include fibers, which are discontinuous strands having a definite length, and filaments, which are continuous strands of material. The nonwoven fabric of the present invention may be formed from staple multicomponent fibers. Such staple fibers may be carded and bonded to form the nonwoven fabric. Preferably, however, the nonwoven fabric of the present invention is made with continuous spunbond multicomponent filaments which are extruded, drawn and laid on a traveling forming surface.

The types of nonwoven materials that may be employed include powder-bonded-carded webs, infrared bonded carded webs, and through-air-bonded-carded webs. The infrared and through-air bonded carded webs can optionally include a mixture of different fibers, and the fiber lengths within a selected fabric web may be within the range of about 1.0 to 3.0 inch and an average bulk density of about 0.02 g/cc to about 0.12 g/cc.

Other suitable absorbent materials for use in the practice of the invention can include materials commonly referred to as superabsorbents. Superabsorbents can be in various forms including particulate and fibrous forms. Known superabsorbent materials include AFA-1 30-53C by Dow Chemical, and W77553 and FAV880A which are commercially available from the Stockhausen Company of Greensboro, N.C. Stockhausen's W77553 is a bulk polymerized polyacrylate with a hydrophobic surface treatment. Stockhausen's FAV880A is a highly crosslinked surface superabsorbent. AFA 130-53C is a 850 to 1400 micron suspension polymerized polyacrylate material available from The Dow Chemical Company of Midland, Mich.

Hydrocolloidal materials, commonly referred to as superabsorbents, can be in the form of a hydrogel-forming polymer composition which is water-insoluble, slightly cross-linked, and partially neutralized. It can be prepared from an unsaturated polymerizable, acid group-containing monomers and cross-linked agents. Such superabsorbents are taught in U.S. Pat. No. 4,798,603 to Meyers et al., U.S. Reissue Pat. No. 32,649 to Brandt et al. and U.S. Pat. No. 4,467,012 to Pedersen et al., as well as in published European Patent Application 0,339,461 to Kellenberger. The disclosures of these patents and the European Patent Application are incorporated by reference herein in their entirety.

Additionally, materials known as "slow rate" superabsorbents can also be used in the practice of the subject invention. By "slow rate" superabsorbent what is meant is a superabsorbent having an absorption time index (ATI) of at least 5 minutes and preferably more than 10 minutes. Adjusting the rate of absorbency of a superabsorbent may be achieved by modifications to the particle size, surface properties, and chemistry of the polymer. Such slow rate superabsorbents are described in greater detail in U.S. Pat. No. 5,843,063 to Anderson et al., the disclosure of which patent is incorporated herein its entirety.

Suitable absorbent materials for use in the practice of the invention may also take the form of absorbent foams such as open cell polyurethane foam, such as disclosed in U.S. Pat. No. 5,853,402 to Faulks et al., the disclosure of which patent is incorporated herein its entirety. Further, starch foams such as disclosed in U.S. Pat. No. 5,506,277 to Griesbach Ill., the disclosure of which patent is incorporated herein its entirety, may also be used.

The invention may also utilize, as suitable absorbent materials, corrugated nonwoven fabrics such as the high bulk corrugated nonwoven fabric disclosed in U.S. Pat. No. 3,668,054 to Stumpf, the disclosure of which patent is incorporated herein its entirety. As disclosed therein, such fabric generally comprises a corrugated web of initially aligned textile fibers implanted in a continuous thin film of a thermoplastic adhesive having an essentially constant thickness. The resulting web-adhesive material is then corrugated to provide the multitude of furrows and grooves, which are irregularly connected near their roots and along their respective sides.

As will be appreciated, appropriate materials for use in the practice of the invention can be variously suitably formed including being meltblown or airlaid or airformed. The term "meltblown fibers" generally refers to fibers formed by extruding a molten thermoplastic material through a plurality of fine, usually circular, die capillaries as molten threads or filaments and into converging high velocity gas (e.g., air) streams which attenuate the filaments of molten thermoplastic material to reduce their diameters. Thereafter, the meltblown fibers are typically carried by the high velocity gas stream and deposited on a collecting surface to form a web of randomly disbursed meltblown fibers. Meltblown fibers may be continuous or discontinuous and are generally tacky when deposited onto a collecting surface. Meltblown materials are described in greater detail in U.S. Pat. No. 5,656,361 to Vogt et al, the disclosure of which is fully incorporated herein by reference.

Further, absorbent member materials of construction which contain or include one or more of various additives such as coagulants, lysing agent or superabsorbents, for example, can also be used. As identified above, adjacent absorbent members will preferably differ in one or more property or characteristic such as chemical composition or construction such as fiber orientation or thickness, for example. In accordance with one preferred embodiment of the invention, such adjacent absorbent members advantageously preferably differ in a selected property or characteristic other than density and such as not easily obtainable with prior art techniques. In particular, the minimization or elimination of horizontal dependency by or between adjacent absorbent layers can result in the utilization of absorbent materials selected for special or particular properties or characteristic.

Moreover, it is to be understood that the broader practice of the invention is not necessarily limited to specific or particular absorbent materials and that other absorbent materials such as are known to those skilled in the art can, if desired, be used. For example, a wide assortment of materials have been designed and developed to better handle or address the various conditions to which such products may be required to perform.

In the practice of the invention, adjacent absorbent members can, if desired, be loosely plied or, if desired, bonded to one another such as via the use of adhesives, thermal or ultrasonic techniques, threading or sewing techniques or other suitable joining technique such as known in the art.

It is be understood that the broader practice of the invention is not necessarily limited to the incorporation of absorbent pad assemblies, such as described above, as the whole or substantially entire absorbent core. For example and as shown in FIGS. 4–10, absorbent articles in accordance with the invention can incorporate such absorbent pad assemblies placed in the central portion of the article with other absorbent elements, including possibly other absorbent materials, plied, folded or otherwise formed adjacent thereto. Further, and shown in FIGS. 11–16, absorbent articles in accordance with the invention can include a central portion which is formed by or includes other absorbent elements with an absorbent pad assembly in accordance with the invention plied, folded or otherwise formed adjacent thereto.

Figure 4:
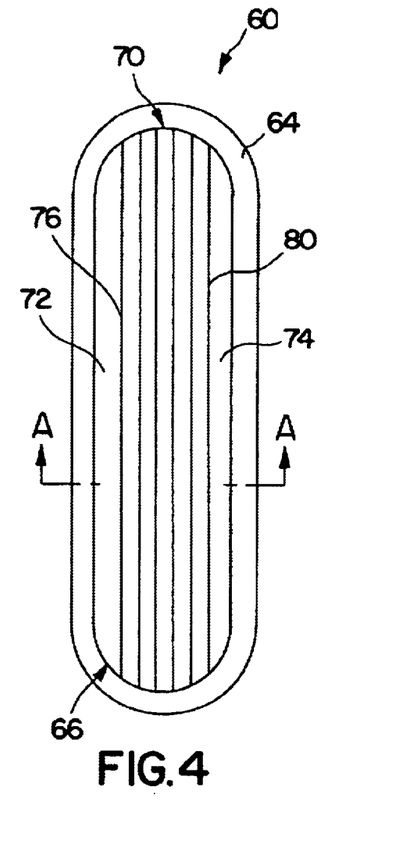
FIGS. 4 and 5 are simplified fragmentary top views of absorbent articles in accordance with alternative embodiments of the invention.
Figure 5:
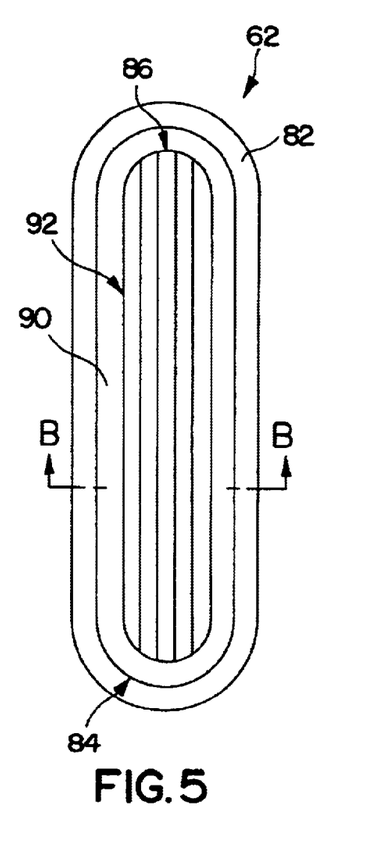

FIGS. 4 and 5 are simplified fragmentary top views of absorbent articles 60 and 62, respectively, in accordance with alternative embodiments of the invention.

As shown in FIG. 4, the absorbent article 60 includes a backsheet 64, an absorbent core 66 and a topsheet (not shown). The absorbent core 66 includes a centrally positioned or placed absorbent pad assembly 70, similar to that described above, and additional absorbent elements 72 and 74 at the first and second longitudinal sides 76 and 80, respectively, thereof. As will be appreciated and as described in greater detail below, the additional absorbent elements 72 and 74 can be continuous or noncontinuous, as may be desired for specific applications.

FIG. 5 illustrates the absorbent article 62 which includes a backsheet 82, an absorbent core 84, and a topsheet (not shown). The absorbent core 84 includes a centrally positioned or placed absorbent pad assembly 86, similar to that described above, with an absorbent element 90 at the perimeter 92 thereof.

Figure 6:
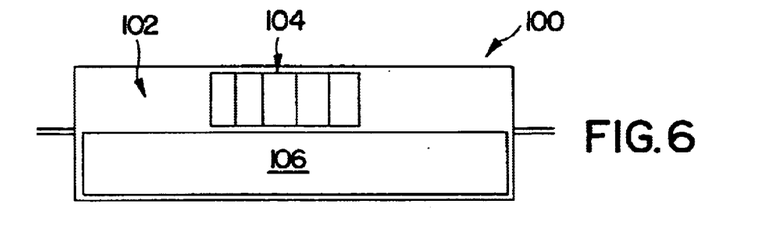
FIGS. 6–10 are simplified sectional alternative side views of absorbent articles taken substantially along the lines A—A and B—B of FIGS. 4 and 5, respectively, and viewed in the direction of the arrows.

FIGS. 6–10 are sectional side views illustrating specific alternative forms for the absorbent articles shown in FIGS. 4 and 5, respectively. For example, FIG. 6 illustrates an absorbent article 100 having an absorbent core 102 wherein an absorbent pad assembly 104, in general accordance with the invention as described above, is placed in overlying fashion with an absorbent element 106.

Figure 7:
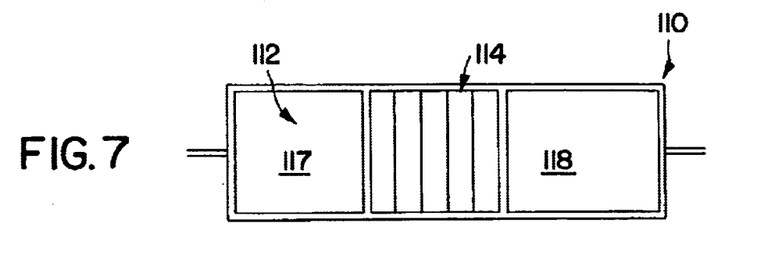

FIG. 7 illustrates an absorbent article 110 having an absorbent core 112 wherein an absorbent pad assembly 114, in general accordance with the invention as described above, is placed in side by side with absorbent elements 117 and 118, respectively. As identified above, the absorbent elements can be formed as a single member or as multiple members, as may be desired for specific applications.

Figure 8:
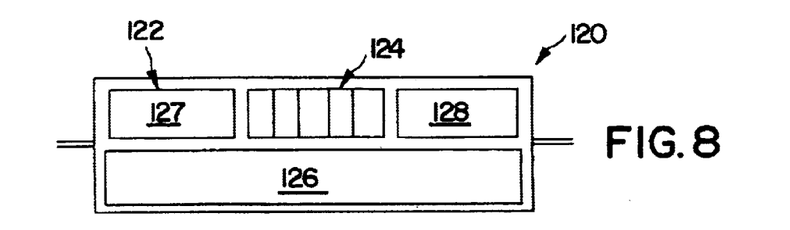
Figure 9:
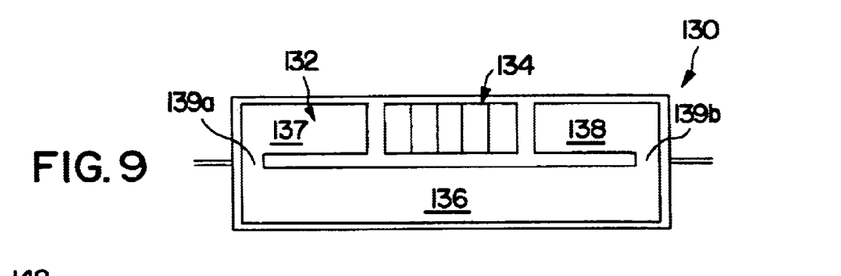
Figure 10:
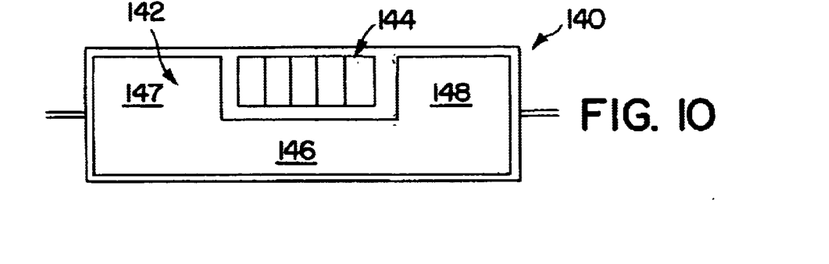

FIGS. 8–10 illustrate specific alternative embodiments combining selected features of the absorbent articles 100 and 110, shown in FIGS. 6 and 7.

More specifically, FIG. 8 illustrates an absorbent article 120 having an absorbent core 122 wherein an absorbent pad assembly 124, in general accordance with the invention as described above, is placed both in overlying fashion with an absorbent element 126 and in side by side with absorbent elements 127 and 128.

FIG. 9 illustrates an absorbent article 130 with an absorbent core 132 including an absorbent pad assembly 134, such as described above. The absorbent article 130 is generally similar to the absorbent article 120 shown in FIG. 8 except that the underlying absorbent element 136 is formed continuous with the side absorbent elements 137 and 138. The side absorbent elements 137 and 138 are folded over at elbow regions 139a and 139b, respectively, to overly the absorbent element 136.

FIG. 10 illustrates an absorbent article 140 with an absorbent core 142 including an absorbent pad assembly 144, such as described above. The absorbent article 140 is generally similar to the absorbent articles 120 and 130 shown in FIGS. 8 and 9, respectively, except that the underlying absorbent element 146 and the side absorbent elements 147 and 148 are formed continuous in a mass having a generally "U-shaped" cross section.

Figure 11:
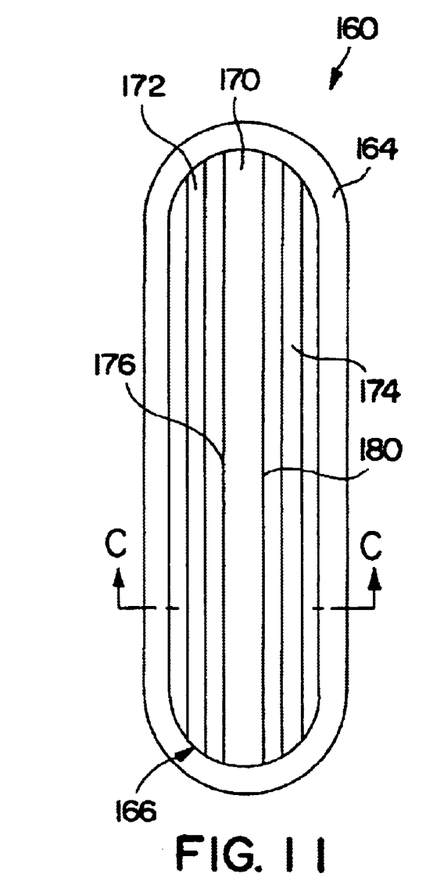
FIGS. 11 and 12 are simplified fragmentary top views of absorbent articles in accordance with still other alternative embodiments of the invention.
Figure 12:
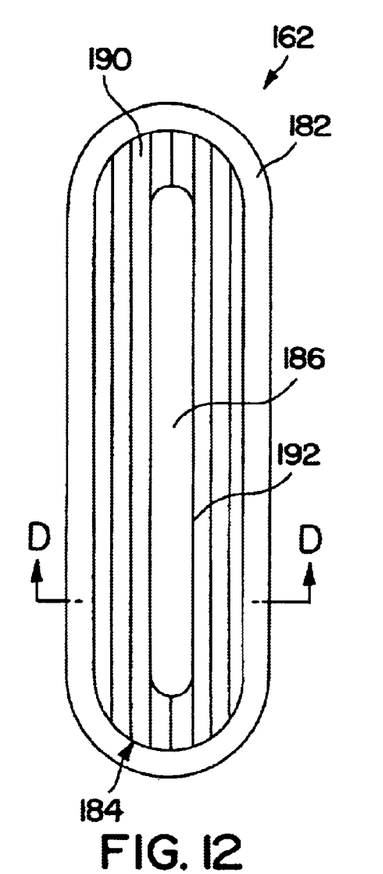

FIGS. 11 and 12 are simplified fragmentary top views of absorbent articles 160 and 162, respectively, in accordance with still other alternative embodiments of the invention.

As shown in FIG. 11, the absorbent article 160 includes a backsheet 164, an absorbent core 166 and a topsheet (not shown). The absorbent core 166 includes a centrally positioned or placed absorbent element 170 with absorbent pad assemblies 172 and 174, similar to that described above, at the longitudinal sides 176 and 180, respectively, thereof.

FIG. 12 illustrates the absorbent article 162 which includes a backsheet 182, an absorbent core 184, and a topsheet (not shown). The absorbent core 184 includes a centrally positioned or placed absorbent element 186 with an absorbent pad assembly 190, similar to that described above, at the perimeter 192 thereof.

Figure 13:
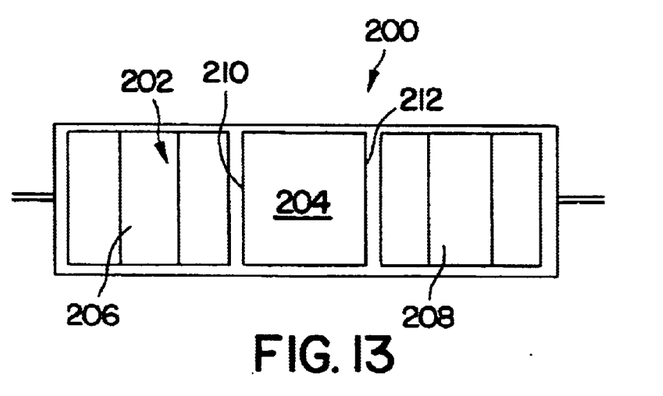
FIG. 13 is a simplified sectional side view of an absorbent article taken substantially along the lines C—C and D—D of FIGS. 11 and 12, respectively, and viewed in the direction of the arrows.

FIG. 13 is a representative sectional side view of absorbent articles such as shown in FIGS. 11 and 12. More specifically, FIG. 13 illustrates an absorbent article 200 having an absorbent core 202 including an absorbent element 204 with absorbent pad assembly first and second portions 206 and 208, each in general accordance with the invention described above. In the cross sectional view of FIG. 13, the absorbent pad assembly portions 206 and 208 are along the longitudinal sides 210 and 212 of the absorbent element 204, respectively. It will be appreciated that the absorbent pad assembly portions 206 and 208 can be parts of a single absorbent pad assembly or separate absorbent pad assemblies, such as described above. More specifically, while FIG. 13 has been described above as being a sectional side view of absorbent articles such as shown in FIG. 12, it will be understood that such an absorbent article structure may be more complicated to manufacture or produce than may be desired. In view thereof, a possibly more process friendly form of such an absorbent article would include an absorbent core element underlying the absorbent element 204 and, such as joining or continuous with either or both the absorbent pad assembly first and second portions 206 and 208.

It is to be understood that various modifications and combinations of the above-described embodiments are possible and are herein encompassed. For example, such possible modifications of the various above-described embodiments can involve the inclusion of one or more overlying or underlying void layer or layer of other selected absorbent article material. More particularly, it may be desirable to include within an absorbent article, in accordance with the invention, a layer of a fluid retention material underlying an absorbent pad assembly, such as described above. In some applications it may be desirable to include a layer of fluid surge material, such as is known in the art, in overlying relation to an absorbent pad assembly, such as described above. Further, the extent of such overlying or underlying, as the case may be, of each such overlying or underlying layer can be partial or complete, as may be desired for a particular application.

Absorbent structures, in accordance with the invention, can be conveniently formed or made by adjacently disposing selected absorbent members, such as described above, and orientating the adjacently disposed absorbent members to provide or otherwise result in a structure having a desired ratio of horizontal width to vertical height. As detailed above, structures in accordance with the invention advantageously include absorbent members having a ratio of horizontal width to vertical height of no more than about 10:1, preferably no more than about 5:1 and, more preferably about 1:1 or less. It is to be understood that the forming or making of such structures may involve the desired selection of one or more desired variables or parameters, such as described above, including: the number, size and shape of adjacently disposed absorbent members as well as the properties, characteristics and materials of construction of such absorbent members, for example, and such as guided by the teachings herein provided.

As will be appreciated, the absorbent members may be initially provided in various orientations such as may or may not require subsequent reorientation. In one particular formation method in accordance with the invention, however, absorbent members are horizontally layered and subsequently vertically reorientated to provide the desired structure.

As described above, adjacent absorbent members can, if desired, be loosely plied or, if desired, bonded to one another such as via the use of adhesives, thermal or ultrasonic techniques, threading or sewing techniques or other suitable joining technique such as known in the art. In accordance with one preferred practice of the invention, such bonding, if used, is preferably done prior to any reorientation, that may be required.

Further, methods for forming such absorbent structures in accordance with the invention may include one or more cutting steps or operations. For example, adjacently disposed absorbent members may be appropriately cut to provide or supply an absorbent pad assembly in a desired selected shape or form such as suitable for the specific use to which such absorbent pad assembly is intended to be applied. Such cutting may occur prior, after or both prior and after orientation as may be desired in specific applications. Various means, such as known in the art, are available whereby such cutting of the adjacently absorbent members can be accomplished including, slit blade and water jet cutting, for example.

While the invention has been described above relative to absorbent articles wherein the absorbent core contains a single absorbent pad assembly in accordance with the invention, it is to be understood that the broader practice of the invention is not necessarily so limited. For example, as will be appreciated by those skilled in the art, the invention can, if desired, be practiced with absorbent articles containing two or other selected multiple of such absorbent pad assemblies. Further, such absorbent articles may contain such two or more absorbent pad assemblies in spaced apart, overlying, partially overlapping or other selected relationship, as may be desired for a particular application.

Thus, the invention provides absorbent pad assemblies, absorbent articles and associated methods which permit the more complete or full utilization of the absorbent capacity thereof as may be desired. The invention also generally provides absorbent pad assemblies, absorbent articles and associated methods which can respond to the possibly wide range of operating and performance conditions to which such assemblies and articles can be exposed and to do so in a more effective and efficient a manner.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

I claim:

1. An absorbent pad assembly comprising:
at least first and second directly adjacent noncontinuous vertically orientated absorbent members, each of the first and second absorbent members having a vertical height with the first and second absorbent members completely horizontally displaced relative to each other along the vertical height of each of the first and second absorbent members and forming a vertically disposed surface interface therebetween,
wherein the first absorbent member is of a different composition than the second absorbent member and wherein the first and second absorbent members are each adapted to absorb a different constituent fluid.

2. The absorbent pad assembly of claim 1 additionally comprising:
a third noncontinuous vertically orientated absorbent member disposed adjacent the second absorbent member opposite the first absorbent member.

3. The absorbent pad assembly of claim 1 wherein the first and second absorbent members each have a width of less than about 20 mm.

4. The absorbent pad assembly of claim 3 wherein the first and second absorbent members each have a width of about 0.5 mm to about 8 mm.

5. The absorbent pad assembly of claim 4 wherein the first and second absorbent members each have a width of about 1 mm to about 5 mm.

6. The absorbent pad assembly of claim 1 wherein the first and second absorbent members each have a width to height ratio of less than 1.

7. The absorbent pad assembly of claim 1 wherein at least one of the first and second absorbent members comprises a surge material.

8. The absorbent pad assembly of claim 1 wherein at least one of the first and second absorbent members comprises a superabsorbent.

9. The absorbent pad assembly of claim 1 wherein at least one of the first and second absorbent members comprises a nonwoven material made up of an airform matrix of thermoplastic polymeric fibers and a multiplicity of individualized wood pulp fibers.

10. The absorbent pad assembly of claim 1 wherein at least one of the first and second absorbent members comprises extruded multicomponent polymeric strands including first and second polymeric components arranged in substantially distinctive zones across the cross-section of the multicomponent strands and extending continuously along the length of the multicomponent strands.

11. The absorbent pad assembly of claim 1 wherein at least one of the first and second absorbent members comprises an absorbent foam.

12. An absorbent article comprising:
a liquid pervious cover on a body-side surface of the article; and
an absorbent pad assembly disposed directly adjacent the cover in underlying relation on a garment-side surface of the cover, the absorbent pad assembly including at least first, second and third generally planar absorbent members, each of the first, second and third absorbent members having a vertical height with the first and second absorbent members directly adjacent and completely horizontally displaced relative to each other along the vertical height of each of the first and second absorbent members and forming a first vertically disposed surface interface therebetween and with the second and third absorbent members directly adjacent and completely horizontally displaced relative to each other along the vertical height of each of the second and third absorbent members and forming a second vertically disposed surface interface therebetween, wherein at least the first absorbent member is of a different composition than the second absorbent member,
wherein at least the first and second absorbent members are each adapted to absorb a different constituent fluid.

13. The absorbent article of claim 12 wherein the first, second and third absorbent members each have a width of less than about 20 mm.

14. The absorbent article of claim 13 wherein the first, second and third absorbent members each have a width of about 0.5 mm to about 8 mm.

15. The absorbent article of claim 14 wherein the first, second and third absorbent members each have a width of about 1 mm to about 5 mm.

16. The absorbent article of claim 12 wherein the first, second and third absorbent members each have a width to height ratio of less than 1.

17. The absorbent article of claim 12 wherein at least one of the first, second and third absorbent members comprises a surge material.

18. The absorbent article of claim 12 wherein at least one of the first, second and third absorbent members comprises a superabsorbent.

19. The absorbent article of claim 12 wherein at least one of the first, second and third absorbent members comprises a nonwoven material made up of an airform matrix of thermoplastic polymeric fibers and a multiplicity of individualized wood pulp fibers.

20. The absorbent article of claim 12 wherein at least one of the first, second and third absorbent members comprises extruded multicomponent polymeric strands including first and second polymeric components arranged in substantially distinctive zones across the cross-section of the multicomponent strands and extending continuously along the length of the multicomponent strands.

21. The absorbent article of claim 12 wherein at least one of the first, second and third absorbent members comprises an absorbent foam.

22. The absorbent article of claim 12 additionally comprising a liquid impervious backsheet on a garment-facing side of the article.

23. The absorbent article of claim 12 wherein the absorbent article is a sanitary napkin.

24. An absorbent article adapted to absorb fluids having a range of constituents, the absorbent article having a contact surface and comprising:

a pad assembly which includes at least first and second directly adjacent noncontinuous absorbent members of different absorbency, the first and second absorbent members generally perpendicularly disposed relative to the contact surface and forming a surface interface therebetween also generally perpendicularly disposed relative to the contact surface and wherein the first absorbent member is adapted to absorb a first constituent fluid and the second absorbent member is adapted to absorb a second constituent fluid different from the first constituent fluid, wherein the first absorbent member is of a different composition than the second absorbent member.

25. The absorbent article of claim 24 wherein at least one of the first and second adjacent noncontinuous absorbent members comprises a surge material.

26. The absorbent article of claim 24 wherein at least one of the first and second adjacent noncontinuous absorbent members comprises a superabsorbent.

27. The absorbent article of claim 24 wherein at least one of the first and second adjacent noncontinuous absorbent members comprises a nonwoven material made up of an airform matrix of thermoplastic polymeric fibers and a multiplicity of individualized wood pulp fibers.

28. The absorbent article of claim 24 wherein at least one of the first and second adjacent noncontinuous absorbent members comprises extruded multicomponent polymeric strands including first and second polymeric components arranged in substantially distinctive zones across the cross-section of the multicomponent strands and extending continuously along the length of the multicomponent strands.

29. The absorbent article of claim 24 wherein at least one of the first and second adjacent noncontinuous absorbent members comprises an absorbent foam.

30. The absorbent article of claim 24 additionally comprising a liquid impervious backsheet on a garment-facing side of the article.

31. The absorbent article of claim 24 additionally comprising a liquid pervious cover on a body-side surface of the article and directly adjacent the pad assembly.

32. The absorbent article of claim 24 wherein the absorbent article is a sanitary napkin.

* * * * *